(12) United States Patent
Noack

(10) Patent No.: US 12,214,112 B2
(45) Date of Patent: Feb. 4, 2025

(54) METHOD FOR CHECKING THE CONVEYING ACCURACY OF CONVEYING DEVICES OF A MEDICAL TREATMENT APPARATUS, AND APPARATUSES

(71) Applicant: Fresenius Medical Care Deutschland GmbH, Bad Homburg (DE)

(72) Inventor: Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 620 days.

(21) Appl. No.: 17/424,717

(22) PCT Filed: Jan. 23, 2020

(86) PCT No.: PCT/EP2020/051645
§ 371 (c)(1),
(2) Date: Jul. 21, 2021

(87) PCT Pub. No.: WO2020/152276
PCT Pub. Date: Jul. 30, 2020

(65) Prior Publication Data
US 2022/0008634 A1   Jan. 13, 2022

(30) Foreign Application Priority Data

Jan. 25, 2019 (DE) .......................... 102019101941.9

(51) Int. Cl.
*A61M 1/16* (2006.01)
*A61M 1/34* (2006.01)
*A61M 1/36* (2006.01)

(52) U.S. Cl.
CPC .......... *A61M 1/1605* (2014.02); *A61M 1/341* (2014.02); *A61M 1/367* (2013.01); *A61M 1/1656* (2013.01); *A61M 2205/3331* (2013.01); *A61M 2205/702* (2013.01)

(58) Field of Classification Search
CPC .... A61M 1/1605; A61M 1/341; A61M 1/367; A61M 1/1656; A61M 2205/3331; A61M 2205/702
USPC ......................................... 210/637, 645, 646
See application file for complete search history.

(56) References Cited

U.S. PATENT DOCUMENTS

| 5,629,871 A | 5/1997 | Love et al. |
| 7,648,476 B2 * | 1/2010 | Bock ................... A61M 1/1601 604/4.01 |
| 2012/0312726 A1 | 12/2012 | Gagel |

(Continued)

FOREIGN PATENT DOCUMENTS

DE    102011106113 A1    1/2013

OTHER PUBLICATIONS

Machine-generated English translation of DE 102011106113, generated on Dec. 19, 2023.*

(Continued)

*Primary Examiner* — Fred Prince
(74) *Attorney, Agent, or Firm* — Fish & Richardson P.C.

(57) ABSTRACT

The present invention relates to a method for checking the conveying accuracy of conveying devices of a blood treatment apparatus. It further relates to a blood treatment apparatus with a control device and/or closed-loop control device, through which the method is effected, a digital storage medium, a computer program product, and a computer program.

26 Claims, 5 Drawing Sheets

(56) References Cited

U.S. PATENT DOCUMENTS

2012/0316799 A1\* 12/2012 Gagel ................ A61M 1/1601
                                                          702/50

OTHER PUBLICATIONS

International Search Report and Written Opinion in International Appln. No. PCT/EP2020/051645, date Apr. 29, 2020, 16 pages (with English translation).

\* cited by examiner

METHOD FOR CHECKING THE CONVEYING ACCURACY OF CONVEYING DEVICES OF A MEDICAL TREATMENT APPARATUS, AND APPARATUSES

CROSS-REFERENCE TO RELATED APPLICATIONS

The present application is the national stage entry of International Patent Application No. PCT/EP2020/051645, filed on Jan. 23, 2020, and claims priority to Application No. 102019101941.9, filed in the Federal Republic of Germany on Jan. 25, 2019, the disclosures of which are expressly incorporated herein in their entireties by reference thereto.

TECHNICAL FIELD

The present disclosure relates to methods for checking the conveying accuracy of conveying devices of a blood treatment apparatus, and a blood treatment apparatus with a control device and/or closed-loop control device. The present disclosure further relates to a digital storage medium, to a computer program product, as well as to a computer program.

BACKGROUND

Various types of blood treatment apparatuses are known. The known blood treatment apparatuses include, for example, the apparatuses for hemodialysis, hemofiltration and hemodiafiltration. During the extracorporeal blood treatment, the blood flows in an extracorporeal blood circuit through a blood treatment unit. In the apparatuses for hemodialysis, hemofiltration and hemodiafiltration, the blood treatment unit is a dialyzer or filter which, in simple terms, is separated by a semipermeable membrane into a blood chamber and a dialysis liquid chamber. During the blood treatment using hemodialysis or hemodiafiltration, the blood flows through the blood chamber while a dialysis liquid flows through the dialysis liquid chamber.

In some blood treatment machines, the dialysis liquid may be produced by volumetric mixing. Volumetric mixing means that at least one liquid is dosed according to the volume. For example, pure water and at least one liquid concentrate may be metered volumetrically and mixed according to a predetermined recipe into fresh dialysis liquid.

With the volumetric metering, the accuracy with which the employed conveying device works is of decisive importance or significance. An incorrect dosage leads to an incorrect composition of the dialysis liquid. The conveying accuracy of a conveying device may change over time. This may be caused by, e.g., leaks, swellings of materials, deposits or collections inside the conveying device and/or in the lines, and wear. While leaks may be reliably detected in an easy way by an automatic integrity test, for example a pressure holding test, other causes that may result in a greater or lesser conveying rate may not be recognizable or apparent, just like that.

To avoid endangering the patient safety, incorrect dosage should be ruled out. Therefore, the conveying devices are designed in such a robust manner that an operation-related change of the conveying rate during their lifetime is as small as possible. Nevertheless, the conveying rate of a conveying device may change over time.

The conveying rate is checked as part of regular maintenance intervals and corrected if necessary. The conveying rate may thereby be determined by incremental filling. Such works are carried out by a qualified service technician.

The more often the conveying devices of the blood treatment apparatus are checked, the more reliably the blood treatment apparatus can work. There is a need for a regular automatic check of the conveying rate. There is a need for an automatic detection of changes in the conveying rate of a conveying device, for example as part of a regular automatic function test.

It is an aspect of the present invention to propose a method for checking the conveying accuracy of conveying devices of a medical treatment apparatus. Further, a control and/or closed-loop control device (in short: control device, which may optionally also control in a closed-loop manner), with which the method may be effected or prompted should be proposed. In addition, further apparatuses suitable for executing the method, e.g., a blood treatment apparatus, should be specified.

SUMMARY

The present disclosure thus proposes a method for quantitatively or qualitatively checking the conveying accuracy of conveying devices from a group of conveying devices. The group consists of a first conveying device, a second conveying device and a third conveying device. They are part of, or functionally connected to, an extracorporeal blood treatment apparatus.

The method encompasses providing a receptacle or container, preferably completely filled with liquid. Air or another gas is preferably not provided in the receptacle. The receptacle is in fluid communication with each of the conveying devices of the group. In this, each conveying device is arranged so that it pumps liquid out of the receptacle.

The method optionally encompasses the complete filling of the receptacle with liquid.

In this, a predetermined initial pressure (or: starting pressure) is optionally set in the receptacle. Said setting may be carried out, purely exemplarily, using filling pumps and/or valves present in lines that fluidly connect the receptacle to its external. For example, by using the filling pump, it can be provided for sufficient liquid pressure inside the receptacle. This may be described as a defined filling, i.e., the pressure prevailing after the filling is known and/or predetermined. It is preferably above the atmospheric pressure.

Further, the method encompasses optionally measuring the pressure prevailing in the closed, liquid-filled receptacle using a first pressure measuring and specifying the measured pressure as initial pressure. However, this first pressure measuring may be omitted, for example if after filling the above-described receptacle with sufficient accuracy, one can assume that the degree or level of the pressure prevailing in the receptacle after the filling is already known, for instance due to the filling process itself. In this case, in all the statements made herein, the pressure prevailing after the filing may be assumed to be known or considered known even without first measuring of the pressure.

The method encompasses actuating a first conveying device of the group. In this, the first conveying device is prompted so that it accomplishes a target conveying activity required with respect to this conveying device in order to convey the predetermined liquid volume out of the receptacle. The conveying activity may consist of a number of strokes, rotations, etc. of the conveying device or of its components, which, e.g., in the light of the design of the conveying device is required to accomplish the needed conveying activity and is referred to herein as target conveying activity. The target conveying activity may describe the conveying activity which is requested or queried by the user or by the control which in turn may correspond to a particular conveying volume. The subsequently actually or effectively performed conveying activity, i.e., for example the actual or real conveyed volume, may deviate respectively. The extent to which the target conveying activity deviates from the actual or real conveying activity may serve for the quantitative information about the accuracy at which the conveying device conveys.

Actuating may also be understood for example as retrieving or requesting the predetermined conveying activity aiming at conveying a target volume or a predetermined target or desired volume out of the receptacle.

Furthermore, the method encompasses measuring, i.e., in a second pressure measurement, the pressure prevailing in the receptacle after the conveying activity of this employed conveying device has been completed, for instance when the target conveying activity has been reached. The pressure being thereby measured is specified or designated as end pressure. If there was a first pressure measuring, see above, this measuring of the end pressure would be the second pressure measuring.

According to the present disclosure, the above-described steps are carried out successively with each conveying device of the group, wherein the end pressure reached after the discharge via the first conveying device is designated as the first end pressure. Optionally, a first pressure difference is determined as being the difference between the initial pressure and the first end pressure and/or further optionally a first compliance is determined. See below for explanations of the term "compliance".

Analogously thereto, for the discharge via the second conveying device, a second end pressure is determined as being the difference between the initial pressure and the second end pressure and/or further optionally, a second compliance is determined.

Therefore, also for the discharge via the third conveying device, a third end pressure and optionally further a third pressure difference being the difference between the initial pressure and the third end pressure are determined and/or further optionally, a third compliance is determined.

According to the present disclosure, a pressure difference between the result of the first pressure measuring and the result of the second pressure measuring is further calculated. Alternatively or additionally, a compliance of the receptacle may be calculated based on these pressure measurings.

Thus, after the conveyance of liquid out of the receptacle via the first conveying device, liquid is conveyed out of the receptacle via the second and subsequently via the third conveying device. Between the discharge via the first and the second conveying device and between the discharge via the second or the third conveying device, the predetermined pressure is preferably adjusted again, respectively.

The method optionally encompasses evaluating at least the first end pressure, second end pressure and third end pressure, preferably with each other, wherein "with each other" may be understood herein as "in an overall view", "in a direct comparison", such as a ranking view.

Additionally or alternatively, the method encompasses an evaluation of at least the first pressure difference, the second pressure difference and the third pressure difference, or at least the first compliance, second compliance or third compliance, likewise preferably with each other.

The result or aim of the evaluation may be to detect a deviation of an actual conveying activity of the first, second and/or third conveying device from the respectively requested target conveying activity, be it quantitatively or qualitatively, wherein a comparison of the deviation between the employed conveying devices may be particularly interesting.

A control device or a closed-loop control device, also referred to herein in short as a control device, is further proposed by the present disclosure. It is configured to prompt or execute, in interaction with a blood treatment apparatus, the method according to the present disclosure.

Further, a blood treatment apparatus (in short: treatment apparatus) is proposed by the present disclosure. The treatment apparatus according to the present disclosure comprises a dialysis liquid system with a receptacle for liquid, a pressure measuring device (i.e., an absolute pressure measuring device) for measuring a pressure prevailing in the receptacle and an evaluation unit being configured, e.g., as described herein, for evaluating end pressures, pressure differences and/or compliances.

Further, the treatment apparatus according to the present disclosure comprises a group of conveying devices which consists of a first conveying device, a second conveying device and a third conveying device, wherein each of the first, second and third conveying devices is in fluid communication with the receptacle.

Furthermore, the treatment apparatus according to the present disclosure comprises a control device or a closed-loop control device, which is configured to, e.g., automatically, prompt, control and/or control in a closed-loop manner the method according to the present disclosure in interaction with further devices or apparatuses of the treatment apparatus, e.g., as disclosed herein.

An interaction may be, or may include, actuating, controlling or controlling in a closed-loop manner. An interaction may be, or may require, a signal communication.

The blood treatment apparatus may for each of the steps mentioned herein comprise a correspondingly suitable and/or configured device like, e.g., an evaluation unit for the evaluation, a pressure measuring device for measuring the pressure, a filling device for the filling of the receptacle (e.g., a pump, a valve or the like) etc.

A storage device according to the present disclosure, e.g., a digital one, e.g., a non-volatile one (denoted here also as carrier), e.g., in the form of a disk, RAM, ROM, CD, hard disk, DVD, USB stick, flash card, SD card, or EPROM, e.g., with electronically or optically readable control signals may be configured such that to configure a control device to a control device with which the method according to the present disclosure described herein may be effected.

In this, all, several or some of the machine-inducible method steps may be prompted.

A computer program product according to the present disclosure comprises a volatile program code or a program code saved on a machine-readable carrier by which a control device is configured such that the method according to the present disclosure described herein may be effected.

In this again, all, several or some of the machine-inducible steps of this method may be prompted.

The term "machine-readable carrier", as used herein, denotes in certain embodiments according to the present disclosure a carrier which contains data or information which is interpretable by software and/or hardware. The carrier may be a data carrier such as a disk, a CD, DVD, a USB stick, a flashcard, an SD card an EPROM and the like.

A computer program according to the present disclosure comprises a program code which configures a control device such that the method according to the present disclosure described herein may be effected.

In this, all, several or some of the machine-inducible steps of this method may be prompted.

According to the present disclosure, a computer program product can be understood as, for example, a computer program which is stored on a data carrier, an embedded system as a comprehensive system with a computer program (e.g., an electronic device with a computer program), a network of computer-implemented computer programs (e.g., a client-server system, a cloud computing system, etc.), or a computer on which a computer program is loaded, run, saved, executed or developed.

According to the present disclosure, a computer program can be understood as for example a physical software product, which is ready for distribution and which has a computer program.

In all of the aforementioned and following statements, the use of the expression "may be" or "may have" and so on, is to be understood synonymously with "preferably is" or "preferably has", and so on respectively, and is intended to illustrate an embodiment.

Whenever numerical words are mentioned herein, the person skilled in the art shall recognize or understand them as indications of numerical lower limits. Hence, unless this leads to a contradiction evident for the person skilled in the art, the person skilled in the art shall comprehend for example "one" as encompassing "at least one". This understanding is also equally encompassed by the present disclosure as the interpretation that a numerical word, for example, "one" may alternatively mean "exactly one", wherever this is evidently technically possible in the view of the person skilled in the art. Both of these understandings are encompassed by the present disclosure and apply herein to all used numerical words.

Whenever the terms "programmed" or "configured" are mentioned herein, it is thus disclosed that these terms are interchangeable.

Advantageous developments of the present invention are each subject-matter of the dependent claims and embodiments.

Whenever an embodiment is mentioned herein, it represents an exemplary embodiment.

Embodiments according to the present disclosure may comprise one or several of the features mentioned supra and/or in the following in any combination which is technically possible.

In some embodiments the term conveying activity encompasses a conveying performance, i.e., for example a conveying volume per conveying duration or time, a conveying rate, a conveying volume per stroke or rotation or the like, a conveying behavior, e.g., when trying to convey a requested volume, a conveying work or effort, a conveying volume, or a conveying of a rated conveying volume.

In some embodiments, the evaluation is carried out while obtaining a measure for the deviation of an actual conveying activity of the first, second and/or third conveying activity from the requested target conveying activity, respectively.

This measure may, for example, be a percentage that indicates what part of the requested target conveying activity is achieved by the actual conveying activity of the first, second and/or third conveying device is different or differs from. The measure may indicate by what percentage the actual conveying activity of one of the conveying devices deviates from the actual conveying activity of another conveying device.

In several embodiments, evaluating encompasses, or consists of, comparing at least one end pressure—being selected from the first, second or third end pressure—or one pressure difference—being selected from the first, second or third pressure difference—with at least one, respectively with one of the other two end pressures or with one, respectively one of the other two pressure differences.

In some embodiments, evaluating encompasses, or consists of, comparing at least one compliance—being selected from the first, second or third compliances—with at least one of the other two compliances.

In certain embodiments, evaluating encompasses, or consists of, determining whether the first end pressure, the second end pressure and/or the third end pressure is within predetermined thresholds, exceeds a minimum value or does not exceed a maximum value.

In several embodiments, evaluating encompasses, or consists of, determining whether the first pressure difference, the second pressure difference and/or the third pressure difference is within predetermined thresholds, exceeds or falls below a threshold, exceeds a minimum value or does not exceed a maximum value.

In some embodiments, evaluating encompasses, or consists of, determining whether the first compliance, the second compliance and/or the third compliance is within predetermined thresholds, exceeds or falls below a threshold, exceeds a minimum value or does not exceed a maximum value.

In several embodiments, evaluating encompasses, or consists of, determining whether a sum, a difference, a product or a quotient between or of two end pressures being selected from the first, the second and the third end pressure, two pressure differences being selected from the first, second and third pressure difference or two compliances being selected from the first, second and third compliance falls below or exceeds a predetermined value.

In some embodiments, actuating at least one conveying device of the group takes place at one first operating point with regard to this conveying device and actuating at least one other conveying device of the group at a second operating point with regard to this very conveying device. The first operating point and the second operating point are different from each other.

In this way, a simultaneous deterioration of the conveying accuracy may be advantageously recognized, e.g., with identically constructed conveying devices. Also this consideration suggests, in some embodiments, checking three conveying devices, but not less, as described herein. Receptacles or containers known from the present technical filed usually comprise, or are connected to, two identically constructed conveying devices, but usually not more than two.

Thus, for example the ultrafiltration pump (it is arranged in order to withdraw liquid out of the extracorporeal blood circuit as tubing set by generating pressure difference), being a conveying device, may convey when checked (as usually otherwise) at maximum conveying rate, since the flow rate is not regularly adjustable in this type of pumps. The natrium pump or the bicarbonate pump may, however, be adjustable and thus be operated at another operating point than for example the ultrafiltration pump. A simultaneous and similar deterioration of the conveying accuracy of the ultrafiltration pump as well as the natrium pump or bicarbonate pump, being differently configured, is highly unlikely.

An operating point (also: bias point or operating condition) may be a specific point in the characteristic diagram or on the characteristic curve of a technical device, which point may be taken or assumed on the basis of the system properties and the acting external influences and parameters.

In some embodiments, it is intended by pairwise comparison between three conveying devices to identify (measured at the other two conveying devices) which conveying device comprises the inaccuracy that led to the fact that the method according to the present disclosure has come to the conclusion that not all the conveying devices comprise the required conveying accuracy.

It is provided in several embodiments, after recognizing the conveying device which does not comprise the required conveying accuracy, to stop or prevent treatment options or other processes or procedures carried out by the blood treatment apparatus which would use the conveying device conveying inaccurately. An alarm or a notification may be supplementarily effected.

In several embodiments of the method, an acoustic and/or optical alarm is emitted in case the evaluation reveals unacceptable results. This includes, e.g., leaving predetermined limit, falling below the lower limit or exceeding the upper threshold, leaving an acceptable value range and/or exceeding a predetermined value.

If a gradual or increasing deterioration in the conveying accuracy of a conveying device is detected at various times over a plurality of (at least two) courses of the method according to the present disclosure, an alarm or a message may in some embodiments be issued in this regard.

For example, the blood treatment apparatus may issue a warning or a notification that maintenance, repair or replacement of the conveying device having insufficient conveying accuracy is due. In this way, a replacement may be made in time, i.e., before the actual total failure occurs, which may advantageously help to reduce the downtime of the blood treatment apparatus. Maintenance or repair of the insufficient conveying device may be planned in advance and thus, unlike a maintenance which is carried out as a reaction, may be carried out only at an inopportune time, i.e., at a possibly inappropriate time.

If the method according to the present disclosure is carried out, as in some embodiments, e.g., before each treatment session during which the blood treatment apparatus is used, or at any narrow time intervals, the point in time at which maintenance or repair of the insufficient conveying device should best be effected can be identified comparatively early. The point in time at which a disturbance of the operation of the blood treatment apparatus will occur due to the insufficient conveying device may advantageously be predictable to a large extent by the method according to the present disclosure using a corresponding evaluation of the gathered measured values or results.

In several embodiments, the results of the method according to the present disclosure (e.g., evaluation results, the deviation from an actual conveying activity, etc.) are displayed or printed, for example, on the blood treatment apparatus (display) or on an external monitor, display or the like.

In several embodiments, the results or at least the results recognized as relevant of the method according to the present disclosure are stored in a data memory in an accessible manner after said method has been executed on the blood treatment apparatus. Said memory data may be part of the blood treatment apparatus and may be for example read out on request. Alternatively, the data memory may be provided on an external device. In this way, results may be for example fed into, a network, and stored there. If necessary, the results may then be accessed from several devices.

In some embodiments, a probability for the occurrence of a disturbance due to malfunction of one or of each conveying device is determined and communicated according to known methods, e.g., by storage in the readable data memory, by display, alarm, etc. In addition or alternatively, the time point or the period of time at which or in which such a disturbance is likely to occur can be determined and communicated.

In several embodiments, known trend analysis methods are used to determine, among other things, the probability of the occurrence of a disturbance due to the malfunction of a conveying device or the time or period of time of said malfunction.

The hardware or software required to carry out the above-mentioned determination of probability, time/period and/or the presentation and/or transmission of the results resulting therefrom is optionally provided and set up, configured and/or programmed accordingly.

Using trend analysis, trends—i.e., medium-term or long-term apparent developments—can be determined and optionally quantified.

Known methods of trend analysis include simple averaging, the determination of moving averages, the determination of the smallest square deviation, first-order exponential smoothing, etc.

In some embodiments of the method, a correction factor for the target conveying activity is automatically provided or given for at least one of the conveying devices of the group, which device is not sufficiently accurately conveying.

An optional correction may be a compensation or a shift such that a future requested target rate is raised by a flat-rate or about the deviation—detected by the present method—between the actual conveying activity and the target conveying activity, alternatively by another suitable factor.

An optional correction may encompass correcting the conveying rate. Correcting may be understood as the correction of a faulty deviation, for example the detected volume difference, determined by a deviation of the end pressure of an expected value of one of the conveying devices, e.g., raising or lowering the conveying rate or conveying activity until a target value is reached. Correcting the conveying rate may be done for example by a control or adjusting action or intervention performed on the conveying device or on the electrical drive of the conveying device.

In some embodiments, actuating a conveying device encompasses or consists of providing or giving or specifying the target activity to at least one of the conveying devices, or for this one, in that at least a number of steps and/or a step angle is predetermined.

In several embodiments, actuating a conveying device encompasses or consists of providing a target conveying activity to at least one of the conveying devices, or for this one, by predetermining at least a number of strokes.

In some embodiments, actuating a conveying device encompasses or consists of predetermining the target conveying activity to at least one of the conveying devices, or for this one, by predetermining a conveying duration or time.

In some embodiments, the receptacle comprises or consists of at least one first and/or one second concentrate supply container and/or sections of the waste water of a balancing system of a blood treatment apparatus. A concentrate supply container may optionally comprise concentrate suction tubes.

In several embodiments, the receptacle comprises or is a section in a liquid line of a dialysis liquid system.

In some embodiments, the receptacle comprises at least one line section. Alternatively, it comprises several line sections being in fluid communication with each other which are part of the blood treatment apparatus, e.g., part of its dialysis liquid system. Such line sections may be connected in fluid communication with each other such that a fluid pressure prevailing therein may adjust itself unhindered within the line network of lines.

In several embodiments, the receptacle is a vessel. All what is stated herein with respect to the receptacle applies in these embodiments unrestrictedly to its design as a vessel as well.

In some embodiments, optionally at least one of the conveying devices of the group is an ultrafiltration pump, optionally one conveying device of said group is a bicarbonate pump and/or optionally at least one conveying device of said group is a natrium pump.

In several embodiments, at least one conveying device of the group is a displacement pump, e.g., a membrane pump, an eccentric membrane pump, a gear pump or a piston pump.

In some embodiments, the first, second and/or third conveying device is a membrane pump, e.g., an eccentric membrane pump, a hose pump or a roller pump.

In several embodiments, the liquid is a dialysis liquid.

Based only on the evaluation of the measuring values of the first pressure measuring and the second pressure measuring, it is at first not possible to determine whether one of the conveying devices conveys inaccurately and to what extent the deviation is. However, it may be determined whether the conveying rate for example of the second conveying device deviates in an unacceptable extent from the conveying rate of the first conveying device or of the third conveying device.

For the ratio between the volume present in the receptacle and the pressure prevailing in the receptacle, respectively, the following applies on the example of the first conveying device:

$$P\_0*V\_0=P\_1*(V\_0-V\_1) \quad (1)$$

wherein again the following applies:

P_0 is the determined initial pressure, an absolute pressure; P_0 may be measured by the first pressure measuring using an absolute pressure gauge or sensor, it may be calculated or be known from other considerations or circumstances or conditions;

P_1 is the pressure prevailing in the receptacle after the completion of the conveying activity of the first conveying device, herein denoted as first end pressure;

V_0 is the initial volume, i.e., the volume encompassed by the interior of the receptacle, when the predetermined initial pressure P_0 prevails therein;

V_1 is the initial volume minus the volume being actually, i.e., effectively, conveyed out of the receptacle by the first conveying device or actually, i.e., effectively.

The liquid volume discharged by the first conveying device, which corresponds to V_0–V_1, could thus be calculated from the above formula (1) in case the initial volume V_0 is known. If the conveyed volume deviates from the volume that the conveying device should have conveyed if it had provided the target conveying activity, then a deviation or inaccuracy of the conveying device can be assumed. However, since the receptacle has a specific compliance, which is why its volume changes depending on pressure changes prevailing in it, the actual values of the expected values, which may result, e.g., from the formula (1), may deviate. This condition is taken into account by the present method in that the one and the same receptacle is, in a predetermined way and thus comparably, filled by three conveying devices and partly emptied by the conveying devices for checking. The influence of for example the compliance of the receptacle is eliminated in this procedure. Its volume does not need to be known.

Based on the above-mentioned considerations, it is recognized that the evaluation of the end pressures P_1, P_2 and P_3, respectively achieved by the three conveying devices, may already answer the question of whether one or more of the three conveying devices conveys inaccurately, which is too high with regard to the other two conveying devices, etc.

This might be the case if, for example, the difference between two of the end pressures (e.g. P_1 and P_3) is within one limit window, but not another difference between two end pressures (e.g. P_1 and P_2). Thus, one could assume that one of the three conveying devices is not sufficiently accurate if the difference between two end pressures is greater that permissible. Similar results may be obtained if, instead of the difference between two end pressures, their sum, quotient or product is considered. The same applies to mathematical relationships, which are set up with the inclusion of such a difference, sum, product or quotient and optionally are also including, e.g., a constant.

Similar conclusions can be drawn when not absolute pressures (here: end pressures), are considered respectively, but relative values, herein pressure differences formed by initial pressure and end pressure.

The first pressure difference $\Delta P\_1$, related to the first conveying device, results here as $$\Delta P\_1 = P\_0 - P\_1 \quad (2)$$

Analogously to this, the above formulas (1) and (2) apply to the second conveying device, wherein P_2 or $\Delta P\_2$ are used rather than P_1 and $\Delta P\_1$. However, P_0 and V_0 also apply for checking the second conveying device, since it is assumed here that the pressure in the receptacle is set again to the predetermined pressure P_0 before checking the second conveying device. This is however an optional embodiment. It may also be assumed that initial pressure values differ from each other, if they are each known.

Just like for the second conveying device, the above formulas (1) and (2) apply also for the third conveying device, wherein this time P_3 or $\Delta P\_3$ are used instead of P_1 or $\Delta P\_1$. P_0 and V_0 in turn also apply when checking the third conveying device.

The first pressure difference, the second pressure difference and the third pressure difference determined in this way may be compared to each other, for example as described in the discussion of the figures by way of example.

As an alternative to the aforementioned calculation of the conveying accuracy using the pressure difference, the former may be checked by a recalculated compliance respectively. An exemplary procedure for this is described below.

Knowing both the predetermined initial pressure P_0—e.g. checked or determined by the first pressure measuring—and the end pressure P_1—e.g., determined by the second pressure measuring—which prevail in the receptacle after discharging the predetermined liquid volume $\Delta V$, the compliance C of the receptacle may be calculated.

$$C = \Delta V / \Delta P \quad (3)$$

Since the respective pressure differences, achieved by the first, second and third conveying devices, should be somehow the same at intact and equally accurately conveying conveying devices, and since in such conveying devices, respectively, the pressure differences resulting from the discharge of about the same amount of conveying volumes are somehow the same, the following applies for the first compliance $$C\_1 = \Delta V/(P\_0 - P\_1),$$

for the second compliance determined by the second conveying device:

$$C\_2 = \Delta V/(P\_0 - P\_2)$$

and for the third compliance determined by the third conveying device:

$$C\_3 = \Delta V/(P\_0 - P\_3).$$

If all three conveying devices are intact and convey at comparable accuracy, then the three calculated values for the compliances C_1, C_2 and C_3 should be the same, at least they do not lie unacceptably far apart from each other.

If, on the other hand, two compliances are unacceptably far apart from each other, which may be determined either absolutely or relative to another difference from two of the three compliances, it can be assumed that the effective conveying volumes deviate to an unacceptable extent from each other since the receptacle should comprise a constant compliance. Further calculations may be advantageously omitted at this point.

In fact, the definition of the compliance according to equation (3) may be used to determine the ΔV of a conveying device based on which the conveying volume failure of the considered conveying device may be calculated by comparing the target conveying activity and the actual conveying activity. However, such a qualitative calculation of the conveying volume failure is not required by the present method. Qualitative determination which may result from simple cross comparisons, may be sufficient therefore allowing to save efforts.

A conveying activity may be discontinuous or continuous. Discontinuous conveyance may mean conveying by repetitive or repeated pump strokes, wherein in turn the conveyance occurs or takes place, however, continuously during a single pump stroke.

Examples of discontinuously conveying devices are membrane pumps and piston pumps. The conveying activity is set in these pumps, which must have a constant stroke volume, by the number of strokes per time unit. A desired conveying volume is conveyed by a certain number of conveying strokes. In this, the cumulative conveying volume should respectively be the same for all pumps.

For example, the first conveying device conveys 1.3 ml at its operating point per stroke, however the second conveying device only 0.65 ml per stroke. In this case, the second conveying device may require two strokes to reach the desired 1.3 ml.

It is preferable to make sure or to take care that all conveying devices convey each the same volume per stroke, even with different stroke volumes. For example, the ultrafiltration pump conveys 1.3 ml per stroke. Then, preferably, the sodium pump must also convey a total of 1.3 ml per cycle, wherein said sodium pump can convey at one time 1.3 ml/stroke or at two times 0.65 ml/stroke per cycle.

Another example of a discontinuous conveying device is a pump with a stepper motor that works stepwise, i.e., discontinuously. The conveying activity may be adjusted in such a pump, for example by using a control unit or a calculating unit specifying a step angle per conveyance step and a number of steps per time unit for stepper motor. A certain conveying volume may be adjusted in such a pump for example using a control unit or a calculating unit specifying a step angle per conveyance step and a number of steps for stepper motor. For achieving an accurate conveyance, it is however advantageous that the pump operates in an occluding manner, such that no backflows can occur.

A continuous conveyance of a certain conveyance volume with a gear pump may be set, for example, by specifying, a speed and a conveyance time to the continuously rotating drive motor, e.g., a brushless DC motor using a control unit or calculating unit.

Since the method described herein is executable with the blood treatment apparatus according to the present disclosure and the treatment apparatus is configured to execute said method by its control device, reference is made to the above-described embodiments in order to avoid repetition.

In some embodiments, while the method according to the present disclosure is in progress or as a step of the method, none of the three conveying devices conveys into the receptacle.

In some embodiments, none of the three conveying devices conveys into the receptacle unless this is used to completely fill the container with liquid.

In some embodiments, none of the three conveying devices conveys into the receptacle unless it is used to set the predetermined initial pressure before the conveying device in question is activated or actuated to provide the flow rate required to discharge the predetermined volume of liquid.

In several embodiments, each of the conveying devices conveys under the method always starting from the same initial pressure. Increasing the pressure in the receptacle using the conveying devices is not intended in these embodiments.

By checking the pumping accuracy, it is meant in several embodiments of the present method checking whether a set pump volume, i.e., the target volume, equals to the volume effectively or actually conveyed, anyhow at least in comparison with the accuracy of further, likewise considered conveying devices.

In some embodiments when checking the three conveying devices, the receptacle is always the same one. The initial pressure prevailing in it may always be the same at the beginning of the conveying activity of each one of the three conveying devices, but this is not necessarily the case.

In several embodiments, no absolute values of a single pressure are considered, but rather relative values of pressures or differences between pressures. Differences between pressures, for instance the difference between an initial pressure and an end pressure, is in some embodiments calculated for each of the three conveying devices.

When measuring a pressure is mentioned herein, this term may in several embodiments also refer to or include determining the desired pressure, for instance by calculating the pressure from present measures.

A treatment apparatus as described herein may, without being limited thereto, be suitable and/or configured for executing a blood treatment, e.g., a hemodialysis, a hemofiltration, a hemodiafiltration or a separation method.

One or several of the herein mentioned advantages may be achieved by some embodiments described herein. Said advantages include the following:

An advantage of the methods and apparatuses described herein is that a blood treatment device is enabled to automatically carry out the checking for sufficient accuracy of the conveying activity of its conveying devices. The service of a qualified service technician or user is not required or may be limited to occasional inspection which may also contribute to cost saving.

In addition, deviations in the conveying activity of a conveying device, which occur for the first time between maintenance visits of the qualified service technician or inspections by the user, may be detected in time or early, for instance as part of a daily routine check.

In this, it is possible without further checking to determine which of the monitored conveying devices deviates in its conveying activity.

Another advantage is the improvement of the user-friendliness of a generic blood treatment apparatus. The user is not charged with checking and correcting the conveying rate of conveying devices. Downtimes of the blood treatment apparatus during the working time of a qualified service technician for checking, such as by weighing or use of measuring cylinders, are not or rarely required. For this purpose, an automatic correction of the conveying settings of the conveying device working or functioning inaccurately may take place.

In addition, the effort required for checking the sufficiency of the conveying accuracy may advantageously be low. Thus, there is no excessive requirement for accuracy, e.g., of the pressure measuring. When comparing the three conveying devices with each other, it is sufficient to make sure that the conveying activities of all conveying devices lie each in an acceptable range.

Since the method according to the present disclosure is established on a defined filling of a receptacle, which will in practice be filled anyway for reasons other than checking the conveying device, part of the work required for the implementation of the present method may advantageously be omitted: at least the first-time filling should already have taken place in many practical applications or uses.

The method according to the present disclosure allows to check the conveying volumes of the pumps without much additional effort. Hence, also possibly occurred damages which influence the pump operation, e.g., detached membranes, for example due to aging processes, may be detected which is, e.g., relevant in eccentric membrane pumps. The number of complex tests of the pumps by a service technician may thus be advantageously reduced or eliminated completely.

Another advantage may thus lie in the increase of the reliability of the blood treatment apparatus, because the more accurately the conveying devices of the blood treatment apparatus convey, the safer it can work for the patient.

Finally, it may be advantageous that conveying devices may be checked by the present method even if there is no mixing chamber, e.g., no mixing chamber with an own monitoring sensor system provided in the blood treatment apparatus, which could be used to check the conveying devices, as this may be the case in several embodiments.

BRIEF DESCRIPTION OF THE FIGURES

The following shall be described with reference to preferred embodiments thereof based on the accompanying drawings. The method and the blood treatment apparatus are described using the example of a hemodialysis apparatus. The method may also be used in the same way with other blood treatment apparatuses, for example with a hemodiafiltration apparatus. The following applies in the figures.

DETAILED DESCRIPTION

Figure 1:
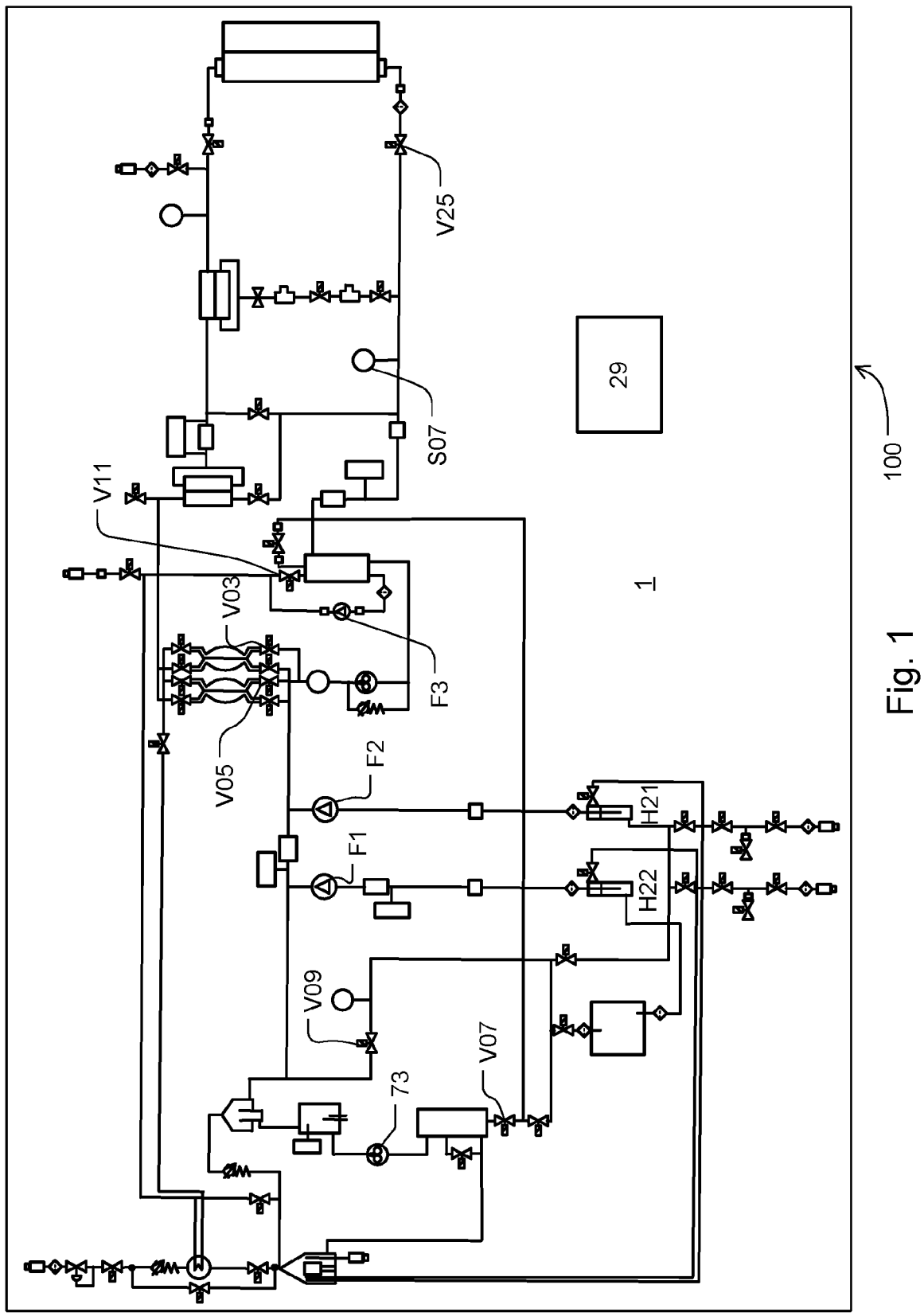
FIG. 1 shows parts of a flow diagram of a dialysis liquid system of a blood treatment apparatus.

FIG. 1 shows parts of a flow diagram of a dialysis liquid system 1 (also referred to as hydraulics) of a blood treatment apparatus 100.

In the dialysis liquid system 1, a plurality of pumps, valves, actuator, sensors and other components are present. All of them may be independently connected to the control device or closed-loop control device 29 in signal communication and may optionally be controlled or read by the latter.

The aforementioned pumps include, amongst others, the bicarbonate pump, which is here exemplarily considered as the first conveying device F1. Further, F2 denotes the natrium pump, which is here considered as the second conveying device, and F3 denotes the ultrafiltration pump which represents the third conveying device.

The conveying devices F1, F2, F3 are present in the dialysis liquid system 1 connected in fluid communication with each other. They are fluidically connected to each other via the lines extracted and shown in bold in FIG. 1a. The lines which connect said conveying devices are fluidically cut off or disconnected from an exterior on one hand by the conveying devices F1, F2, F3 and on the other hand by valves V03, V05, V07, V09, V11, V25. The volume limited by the aforementioned conveying devices F1, F2, F3 and valves V03, V05, V07, V09, V11, V25 results therefore in a sealed vessel or a composite of sealed but communicating lines or vessels and is referred to herein as receptacle. Other terms, such as volume, liquid receiving section, etc. would also be conceivable by the present disclosure instead of "receptacle".

Figure 1A:
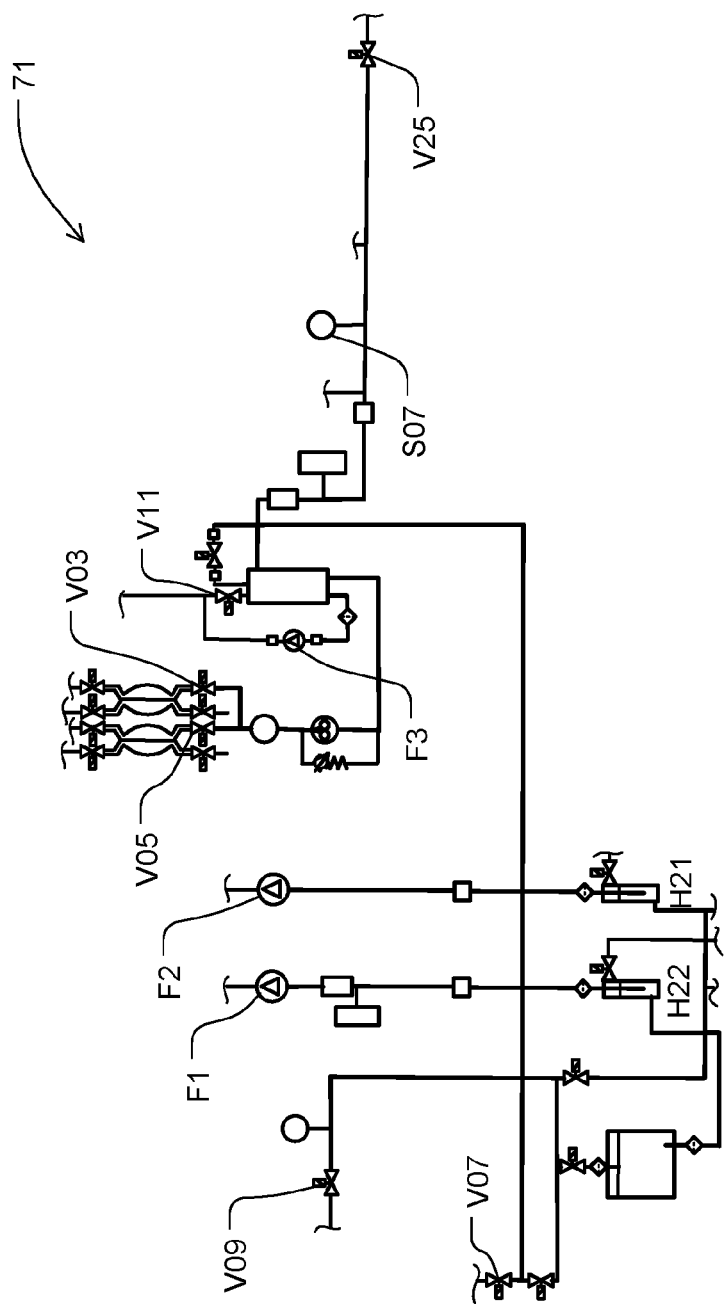
FIG. 1a shows a section of FIG. 1, which section is limited to the receptacle shown in FIG. 1.

The receptacle in FIG. 1a shown by omitting or not illustrating those elements of FIG. 1 not involved in establishing its sealed volume, is referred to herein as receptacle 71, see FIG. 1a.

The three conveying devices F1, F2, F3 are arranged with respect to the receptacle 71 such that they can convey the liquid present in the receptacle 71 out of the latter, which they sequentially do when the method is in process.

The pressure gauge present in the receptacle with or by which, e.g., the first and the second pressure measuring may be carried out, is designated in FIG. 1 with S07. Like any other pressure sensor used, this pressure gauge may have the highest measuring accuracy of all pressure gauges present in the receptacle. Other pressure gauges than the pressure sensor S07 described here are alternatively also possible. The pressure gauge used may be an analog-to-digital converter (ADC).

FIG. 1a shows the receptacle already shown in FIG. 1. The components not involved in establishing the sealed receptacle 71 which are not shown in FIG. 1 are not shown again in FIG. 1a for better clarity.

Figure 1B:
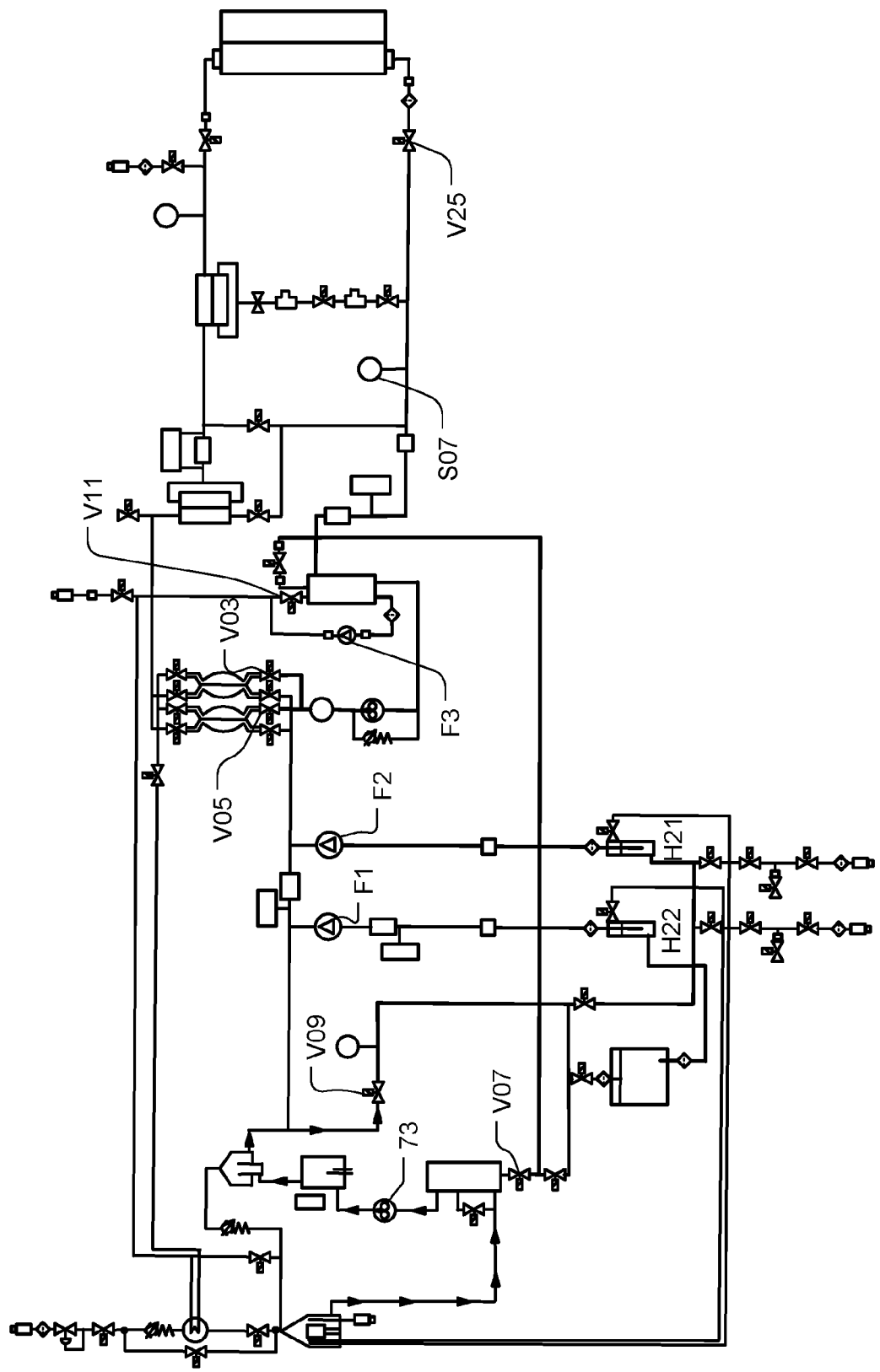
FIG. 1b shows the parts of the flow diagram of FIG. 1 with a clarifying illustration of a filling.

FIG. 1b shows the parts of the flow diagram of FIG. 1. The FIG. 1b clarifies or illustrates by the drawn arrows a first filling of the receptacle 71 such that it preferably contains only liquid, but not also gas. This may be done by a liquid source 73 which is likewise in fluid communication with the receptacle 71. The same applies for a refilling, after the first or the second conveying device F1, F2 has each conveyed a conveying volume out of the receptacle 71 when executing the method according to the present disclosure.

In some embodiments, the filling may be done optionally also from an external source, for example a liquid bag.

Through the filling, an initial pressure is defined within the receptacle 71. This initial pressure may be adjusted or set by the use of the liquid source 73, alternatively or additionally, for example also via the valve V11, e.g., when the filling is done via a pump in an undefined manner. In FIG. 1b, the filling takes place by opening the valve V09. The same applies to a refilling as described supra. Thereby, the other valves limiting the receptacle 71 are optionally closed.

Optionally, each valve connected to the receptacle 71 may therefore be opened for the filling and closed again, in which case the other valves of the receptacle 71 are preferably closed.

Figure 2:
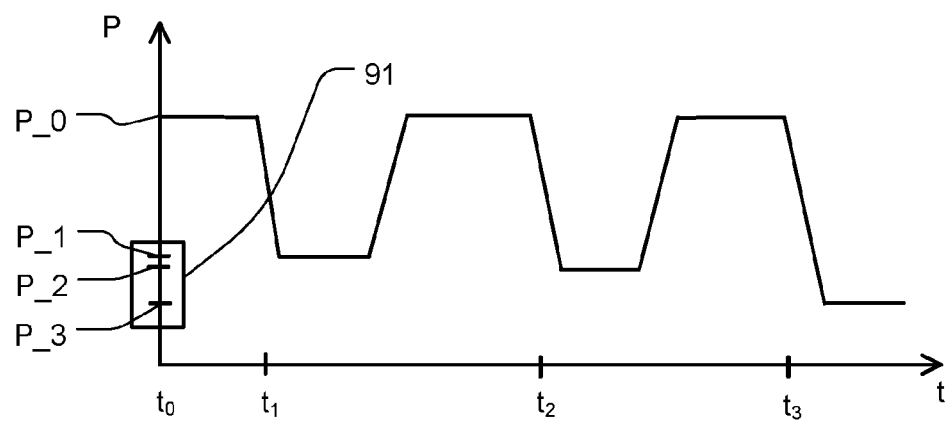
FIG. 2 shows an exemplary course of the method in a pressure-time diagram.

FIG. 2 shows an exemplary course of the method according to the present disclosure in a diagram of pressure [P] over time [t].

The method starts at t0, after the initial pressure P_0 has been set in the receptacle 71, which may take place by the liquid source 73 and may possibly be checked or monitored by the pressure gauge S07.

At the time point t1, the first conveying device F1 conveys liquid out of the receptacle according to the controlled conveying activity of this conveying device, upon which or for which reason the pressure gauge S07 or another pressure sensor detects or determines a drop of the pressure prevailing in the receptacle 71 to P_1, the first end pressure, after the first conveying device has completed the discharge of liquid.

After discharging liquid by the first conveying device F1 and after the pressure P_1 resulting in the receptacle 71 thereupon has been determined, the pressure is again set to the initial pressure P_0.

At time point t2, the second conveying device F2 now conveys which is why a pressure P_2 which is reduced compared to the initial pressure P_0 is set in the receptacle 71 as a new, second end value.

After refilling the receptacle 71 such that the initial pressure P_0 prevails again, the third conveying device F3 conveys liquid out of said receptacle 71 which leads to a new, third end pressure P_3.

The evaluation of the three end pressures P_1, P_2 and P_3 shows that although the P_1 and P_2 are indeed quite close to each other, but not the third end pressure P_3.

Since the receptacle 71 exhibited constant or unchanged compliance during the checking of the three conveying devices F1, F2 and F3 and comprised a constant liquid volume (here exemplarily at an always identical initial pressure P_0), the second conveying device F2 has conveyed slightly less liquid out of the receptacle 71 than the first conveying device F1, but significantly more than the third conveying device F3.

The evaluation of the three end pressures P_1, P_2 and P_3 may be (or encompass) the answer to the question whether the three end pressures are within a threshold window 91 or not. If they are all within the predetermined threshold window 91, then it may for this case be for example determined that the conveying accuracy of none of the three conveying devices F1, F2 and F3 deviates from the permissible measure. However, if the spread between any two end pressure values would be greater than the extent of the threshold window 91 so that not all three end pressures could be encompassed therein, then one would assume an inadmissible deviation of at least one of the three conveying devices. Possibly, the third conveying device F3 has conveyed more than it should have. An alarm could be provided for this case. Such an alarm could already encompass the notification as to which of the conveying devices F1, F2 and F3 deviates, with regard to its accuracy, from the other two conveying devices.

In this, it is of importance that it does not have to be determined a priority where the threshold window has to lie, i.e., which absolute pressure value determines its lower limit, and which absolute pressure value determines its upper limit. It is sufficient to determine how far the end pressure of one of the conveying devices may deviate from the end pressure of one of the other two conveying devices. Changes, which relate to the volume of the receptacle, the compliance of the receptacle, which may change, e.g., after replacement of a line in the course of maintenance or repair, etc. have no influence on the method according to the present disclosure. There is no need to communicate such changes to the system, which helps to keep the effort low, for example after a maintenance.

Figure 3A:
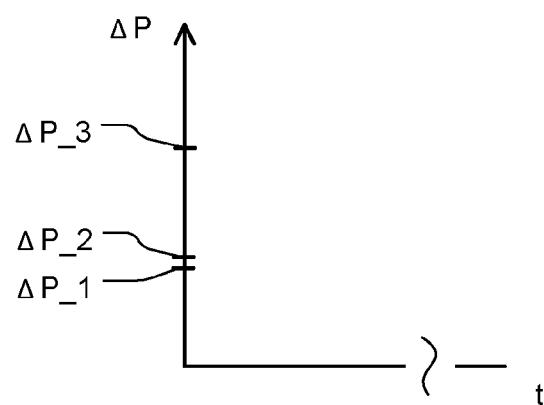
FIG. 3a shows an exemplary course of the method of a further embodiment in which the pressure differences are considered.

FIG. 3a shows the basis for the alternative evaluation based on the end pressures P_1, P_2 and P_3 assumed in FIG. 3. In this alternative evaluation, it is not the relative position of the three end pressures which is considered, rather the relative position of the three pressure differences ΔP_1, ΔP_2, ΔP_3 are compared to each other. Thus, the pressure differences are here compared to each other, each resulting as a difference between initial pressure P_0 and the respective end pressure. It can again be seen that a pressure difference, namely that achieved with the third conveying device, differs most.

Figure 3B:
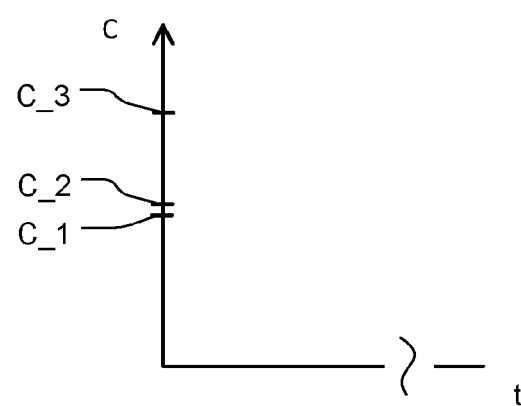
FIG. 3b shows an exemplary course of the method of a further embodiment in which calculated compliances are considered for evaluation.

FIG. 3b shows the basis for a further alternative evaluation based on the end pressures P_1, P_2 and P_3 assumed in FIG. 3. In this alternative evaluation, it is not the relative position of the three end pressures which is considered, rather the relative position of the three compliances C_1, C_2 and C_3 are compared to each other. Thus, the compliances calculated as explained supra are here compared to each other. Said relative position should be the same within acceptable tolerances. It can be seen again that a compliance C, namely the one calculated for the discharge using the third conveying device F3, differs most.

The evaluation for the embodiments shown in FIGS. 3a and 3b may be carried out as described herein.

LIST OF REFERENCE NUMERALS 100 blood treatment apparatus
1 dialysis liquid system
29 control device or closed-loop control device
71 receptacle or receptacle
73 liquid source
91 threshold window
F1 first conveying device, here exemplarily: bicarbonate pump
F2 second conveying device, here exemplarily: natrium pump
F3 third conveying device, here exemplarily: ultrafiltration pump
S07 pressure gauge or sensor
V03 valve V05 valve
V07 valve
V09 valve
V11 valve
V25 valve
H21 first concentrate supply container
H22 second concentrate supply container
P_0 initial pressure
P_1 first end pressure
P_2 second end pressure
P_3 third end pressure
ΔP_1 first pressure difference
ΔP_2 second pressure difference
ΔP_3 third pressure difference
C compliance
C_1 first compliance
C_2 second compliance
C_3 third compliance
t time

The invention claimed is:

1. A method for checking or monitoring conveying or conveyance accuracy of conveying devices of a group of conveying devices, the group consisting of: a first conveying device, a second conveying device, and a third conveying device of a blood treatment apparatus for the extracorporeal blood treatment, the method comprising:
   a) providing a completely liquid-filled receptacle which is in fluid communication with every conveying device of the group of conveying devices;
   b) setting a predetermined initial pressure in the receptacle or measuring the pressure prevailing therein by a first pressure measurement and defining the measured pressure as an initial pressure, wherein the initial pressure corresponds to the receptacle being completely liquid-filled;
   c) actuating one conveying device of the group of conveying devices such that the one conveying device accomplishes a target conveying activity required with respect to the one conveying device in order to convey a predetermined liquid volume out of the receptacle; and
   d) measuring, in a second pressure measurement, the pressure prevailing in the receptacle after the target conveying activity of the one conveying device has been completed, wherein the second pressure measurement is an end pressure,
   wherein:
      the sequence of steps a) to d) is carried out successively for each conveying device of the group of conveying devices, wherein the predetermined initial pressure is the same for each sequence of steps performed by each of the conveying devices of the group of conveying devices,
      for conveying by the first conveying device a first end pressure is determined, a first pressure difference between the initial pressure and the first end pressure is determined, and/or a first compliance is determined, the first compliance being a ratio of a change of liquid volume in the container caused by the first conveying device and the first pressure difference,
      for conveying by the second conveying device a second end pressure is determined and a second pressure difference between the initial pressure and the second end pressure is determined and/or a second compliance is determined, the second compliance being a ratio of a change of liquid volume in the container caused by the second conveying device and the second pressure difference, and
      for conveying by the third conveying device a third end pressure is determined, a third pressure difference between the initial pressure and the third end pressure, and/or a third compliance is determined, the third compliance being a ratio of a change of liquid volume in the container caused by the third conveying device and the second pressure difference; and
   the method further comprises: in response to determining that (i) at least one of the first end pressure, the second end pressure or the third end pressure falls outside a first predetermined range or value, (ii) at least one of the first pressure difference, the second pressure difference or the third pressure difference falls outside a second predetermined range or value, or (iii) at least one of the first compliance, the second compliance or the third compliance falls outside a third predetermined range or value: (i) emitting an acoustic and/or optical alarm, or (ii) stopping or preventing the extracorporeal blood treatment from being carried out by the blood treatment apparatus.

2. The method according to claim 1, wherein determining that (i) at least one of the first end pressure, the second end pressure or the third end pressure falls outside a first predetermined range or value, (ii) at least one of the first pressure difference, the second pressure difference or the third pressure difference falls outside a second predetermined range or value, or (iii) at least one of the first compliance, the second compliance or the third compliance falls outside a third predetermined range or value is carried out while obtaining a measure for the deviation of the actual conveying activity of the first, second and/or third conveying device from the respectively requested target conveying activity.

3. The method according to claim 1, further comprising comparing the first, second and third end pressure, or the first, second and third pressure difference, or the first, second and third compliance, with each other.

4. The method according to claim 1, wherein actuating at least one conveying device of the group of conveying devices takes place at a first operating point related to the at least one conveying device, and wherein actuating at least one other conveying device from the group of conveying devices takes place at a second operating point related to the at least one other conveying device, wherein the first operating point and the second operating point differ from each other.

5. The method according to claim 1, wherein falling outside the predetermined range or value comprises leaving predetermined thresholds, falling below a lower limit of the predetermined range, exceeding an upper limit of the predetermined range, leaving an acceptable value range, and/or exceeding a predetermined value.

6. The method according to claim 1, further comprising an additional step of automatically providing a correction factor for the target conveying activity for at least one of the conveying devices of the group of conveying devices.

7. The method according to claim 1, wherein actuating a conveying device comprises:
   specifying the target conveying activity for at least one of the conveying devices by specifying at least a number of steps and/or a step angle, and/or
   specifying the target conveying activity for at least one of the conveying devices by specifying at least a number of pump strokes, and/or specifying the target conveying activity for at least one of the conveying devices by specifying a conveying duration.

8. The method according to claim 1, wherein the receptacle comprises or consists of at least a first concentrate supply container and/or a second concentrate supply container and/or sections of a waste water branch of a balancing system.

9. The method according to claim 1, wherein the receptacle comprises a section within a liquid line of a dialysis liquid system.

10. The method according to claim 1, wherein at least one conveying device of the group of conveying devices is embodied as an ultrafiltration pump, bicarbonate pump and/or a natrium pump.

11. The method according to claim 1, wherein at least one conveying device of the group of conveying devices is a positive displacement pump, wherein the displacement pump is one of: a membrane pump, eccentric membrane pump, hose pump, roller pump, gear pump or piston pump.

12. A control device or a closed-loop control device, configured in order to prompt or execute the method according to claim 1 in interaction with a blood treatment apparatus.

13. A digital storage medium with electronically readable control signals, configured for configuring a control and/or closed-loop control device to a control and/or closed-loop control device by which the method may be prompted according to claim 1.

14. A computer product with a program code saved on a machine-readable carrier for configuring a control and/or closed-loop control device to a control and/or closed-loop control device by which the method may be prompted according to claim 1.

15. A computer program with a program code for configuring a control and/or closed-loop control device to a control and/or closed-loop control device by which the method may be prompted according to claim 1.

16. A blood treatment apparatus comprising:
a dialysis liquid system comprising a receptacle for containing liquid;
a pressure measuring device for measuring a pressure prevailing in the receptacle;
an evaluation unit configured for evaluating end pressures, pressure differences and/or compliances;
a group of conveying devices which consists of: a first conveying device, a second conveying device and a third conveying device, wherein each of the conveying devices of the group of conveying devices is in fluid communication with the receptacle; and
a control device or a closed-loop control device according to claim 12 and configured for prompting execution of a method for checking conveying activity of the first conveying device, of the second conveying device and of the third conveying device, the method comprising:
setting a predetermined initial pressure in the receptacle while the receptacle is closed and completely liquid-filled, or measuring a pressure prevailing therein by a first pressure measurement and defining the measured pressure as an initial pressure, wherein the initial pressure corresponds to the receptacle being completely liquid-filled;
actuating one conveying device of the group of conveying devices such that it accomplishes a target conveying activity required with respect to the one conveying device in order to convey a predetermined liquid volume out of the receptacle; and
measuring, in a second pressure measurement, the pressure prevailing in the receptacle after the conveying activity of the one conveying device has been completed, wherein the measured pressure is an end pressure, wherein:
the setting, the actuating, and the measuring is carried out successively for each conveying device of the group of conveying devices, wherein the predetermined initial pressure is the same for each sequence of steps performed by each of the conveying devices of the group of conveying devices,
for conveying by the first conveying device a first end pressure is determined, a first pressure difference between the initial pressure and the first end pressure is determined, and/or a first compliance is determined, the first compliance being a ratio of a change of liquid volume in the container caused by the first conveying device and the first pressure difference,
for conveying by the second conveying device a second end pressure is determined and a second pressure difference between the initial pressure and the second end pressure is determined and/or a second compliance is determined, the second compliance being a ratio of a change of liquid volume in the container caused by the second conveying device and the second pressure difference, and
for conveying by the third conveying device a third end pressure is determined, a third pressure difference between the initial pressure and the third end pressure, and/or a third compliance is determined, the third compliance being a ratio of a change of liquid volume in the container caused by the third conveying device and the second pressure difference; and
the method further comprises: in response to determining that (i) at least one of the first end pressure, the second end pressure or the third end pressure falls outside a first predetermined range or value, (ii) at least one of the first pressure difference, the second pressure difference or the third pressure difference falls outside a second predetermined range or value, or (iii) at least one of the first compliance, the second compliance or the third compliance falls outside a third predetermined range or value: (i) emitting an acoustic and/or optical alarm, or (ii) stopping or preventing the extracorporeal blood treatment from being carried out by the blood treatment apparatus.

17. The blood treatment apparatus according to claim 16, wherein the evaluation unit is configured such that the determination that (i) at least one of the first end pressure, the second end pressure or the third end pressure falls outside a first predetermined range or value, (ii) at least one of the first pressure difference, the second pressure difference or the third pressure difference falls outside a second predetermined range or value, or (iii) at least one of the first compliance, the second compliance or the third compliance falls outside a third predetermined range or value is carried out while obtaining a measure for the deviation of an actual conveying activity of the first, second and/or third conveying device from the controlled target conveying activity.

18. The blood treatment apparatus according to claim 16, wherein the evaluation unit is further configured to compare (1) the first end pressure, second end pressure, and the third end pressure with each other, or (2) the first pressure difference, second pressure difference, and the third pressure difference, or (3) the first compliance, the second compliance, and the third compliance with each other.

19. The blood treatment apparatus according to claim 16, wherein actuating at least one conveying device of the group of conveying devices takes place at a first operating point related to the at least one conveying device, and wherein actuating at least one other conveying device from the group of conveying devices takes place at a second operating point related to the at least one other conveying device, wherein the first operating point and the second operating point differ from each other.

20. The blood treatment apparatus according to claim 16, wherein falling outside the predetermined range or value comprises leaving predetermined thresholds, falling below a lower limit of the predetermined range, exceeding an upper limit of the predetermined range, leaving an acceptable value range, or exceeding a predetermined value.

21. The blood treatment apparatus according to claim 16, further configured for automatically providing a correction factor for the target conveying activity for at least one of the conveying devices from the group of conveying devices.

22. The blood treatment apparatus according to claim 16, wherein actuating a conveying device comprises:
specifying the target conveying activity for at least one of the conveying devices by specifying at least a number of steps and/or a step angle, and/or,
predetermining the target conveying activity for at least one of the conveying devices by specifying at least a number of strokes, and/or,
predetermining the target conveying activity for at least one of the conveying devices by specifying a conveying duration.

23. The blood treatment apparatus according to claim 16, wherein the receptacle comprises or consists of at least a first concentrate supply container and/or a second concentrate supply container and/or sections of a water branch of a balancing system.

24. The blood treatment apparatus according to claim 16, wherein the receptacle is or encompasses a section in a liquid line of a dialysis liquid system.

25. The blood treatment apparatus according to claim 16, wherein at least one conveying device of the group of conveying devices is embodied as an ultrafiltration pump, a bicarbonate pump and/or a natrium pump.

26. The blood treatment apparatus according to claim 16, wherein at least one conveying device of the group of conveying devices is a positive displacement pump, wherein the displacement pump is a membrane pump, eccentric membrane pump, hose pump, roller pump, gear pump or a piston pump.

* * * * *